(12) United States Patent
Shah et al.

(10) Patent No.: US 8,841,457 B2
(45) Date of Patent: Sep. 23, 2014

(54) PROCESS FOR CYCLOOXYGENASE-2 SELECTIVE INHIBITOR

(75) Inventors: Dharmesh Mahendra Shah, Mumbai (IN); Sanjay Amratlal Solanki, Mumbai (IN); Viral Narendra Jariwala, Surat (IN); Ashok Vasantray Vyas, Vadadora (IN); Ashokkumar Bhikhubhai Mistry, Navsari (IN)

(73) Assignee: Virdev Intermediates Pvt. Ltd., Gujarat (IN)

( * ) Notice: Subject to any disclaimer, the term of this patent is extended or adjusted under 35 U.S.C. 154(b) by 0 days.

(21) Appl. No.: 13/885,522

(22) PCT Filed: Nov. 15, 2011

(86) PCT No.: PCT/IN2011/000791
§ 371 (c)(1), (2), (4) Date: May 15, 2013

(87) PCT Pub. No.: WO2012/066570
PCT Pub. Date: May 24, 2012

(65) Prior Publication Data
US 2013/0245272 A1    Sep. 19, 2013

(30) Foreign Application Priority Data

Nov. 15, 2010  (IN) .................... 3121/MUM/2010

(51) Int. Cl.
| | | |
|---|---|---|
| *A01N 43/40* | (2006.01) | |
| *A61K 31/44* | (2006.01) | |
| *C07D 213/04* | (2006.01) | |
| *C07D 213/26* | (2006.01) | |
| *C07D 211/70* | (2006.01) | |
| *C07D 211/82* | (2006.01) | |
| *C07D 213/46* | (2006.01) | |
| *C07D 213/50* | (2006.01) | |
| *C07D 213/61* | (2006.01) | |

(52) U.S. Cl.
CPC ............ *C07D 213/61* (2013.01); *C07D 213/50* (2013.01)
USPC .......... 546/259; 514/332; 514/334; 514/354; 514/355; 546/255; 546/258; 546/315

(58) Field of Classification Search
USPC .......................................... 514/334; 546/259
See application file for complete search history.

(56) References Cited

U.S. PATENT DOCUMENTS

| | | |
|---|---|---|
| 5,861,419 A | 1/1999 | Dube et al. |
| 6,001,843 A | 12/1999 | Dube et al. |

(Continued)

FOREIGN PATENT DOCUMENTS

| | | |
|---|---|---|
| WO | 99/55830 | 11/1999 |
| WO | 2005120584 | 12/2005 |
| WO | 2010097802 | 9/2010 |

OTHER PUBLICATIONS

Davies; J. Org. Chem. 2000, 65, 8415-8420.*

(Continued)

*Primary Examiner* — John Mabry
*Assistant Examiner* — Daniel Carcanague
(74) *Attorney, Agent, or Firm* — Kramer Amado, P.C.

(57) ABSTRACT

The present invention describes a process for preparing a cyclooxygenase-2 selective inhibitor. It provides a synthetic procedure for the said substance namely 5-chloro-3-(4-methylsulphonyl)phenyl-2-(2-methyl-5-pyridinyl)pyridine of formula (I). The invention also relates to preparation of a new intermediate of formula (IV) and a process to prepare it. Furthermore, the invention describes a process for preparing another key intermediate of formula (II). Compounds of formula (IV) and formula (II) are useful intermediates in synthesis of the said cyclooxygenase-2 inhibitor.

16 Claims, 4 Drawing Sheets

(I)

(II)

(III)

(IV)

(V)

(VI)

(56) References Cited

U.S. PATENT DOCUMENTS

| | | | |
|---|---|---|---|
| 6,040,319 A | 3/2000 | Corley et al. | |
| 6,071,936 A | 6/2000 | Dube et al. | |
| 6,596,736 B2 | 7/2003 | Dube et al. | |
| 6,600,046 B2 * | 7/2003 | Bessard et al. | 546/315 |
| 6,812,346 B2 | 11/2004 | Dube et al. | |

OTHER PUBLICATIONS

Sato; Tetrahedron 57 (2001) 2469-2476.*

Marcoux; Organic Letters, 2000, 2, 2339-2341.*

Majo; Bioorganic & Medicinal Chemistry Letters (2005), 15(19), 4268-4271.*

Caturla, F et al., "Racemic and chiral sulfoxides as potential prodrugs of the COX-2 inhibitors Vioxx<(>R) and Arcoxia<(>R)", Bioorganic & Medicinal Chemistry Letters, vol. 16, No. 12., Jun. 15, 2006, 3209-3212 (Abstract Only).

International Search Report issued for PCT/IN2011/000791 dated May 16, 2012.

* cited by examiner

PROCESS FOR CYCLOOXYGENASE-2 SELECTIVE INHIBITOR

FIELD OF INVENTION

The present invention relates to a process for synthesis of cyclooxygenase-2 selective inhibitor. More particularly, the invention relates to a process for synthesis of 5-Chloro-3-(4-methylsulphonyl)phenyl-2-(2-methyl-5-pyridinyl)pyridine of the following Formula I from novel compound of formula (IV).

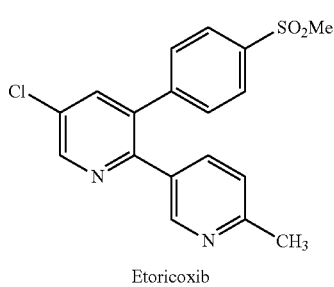

Etoricoxib

[Formula (I)]

The invention further provides a novel compound (IV) and its process of preparation thereof. The invention also relates to preparation of compound of Formula (II), useful in synthesis of said cyclooxygenase-2 inhibitor.

BACKGROUND AND PRIOR ART

Cyclooxygenase-2 selective inhibitors constitute an important class of non-steroidal anti-inflammatory drug substances (NSAIDs), especially due to their improved safety profile. Commonly used NSAIDs, for example aryl propionic acid or aryl acetic acid derivatives are known to cause gastric irritation and ulceration upon prolonged use of such drugs. Cyclooxygenase-2 inhibitors, which act on mechanism of isozyme expression in inflamed tissues, show better safety in this regard.

Etoricoxib selectively inhibits isoform 2 of cyclooxygenase enzyme (COX-2) and currently it is approved in more than 70 countries for therapeutic indications like treatment of rheumatoid arthritis, psoriatic arthritis, ankylosing spondylitis, chronic low back pain, acute pain, osteoarthritis and gout.

Compounds of general formula (A) including Etoricoxib are disclosed in U.S. Pat. No. 5,861,419 as depicted in the following scheme.

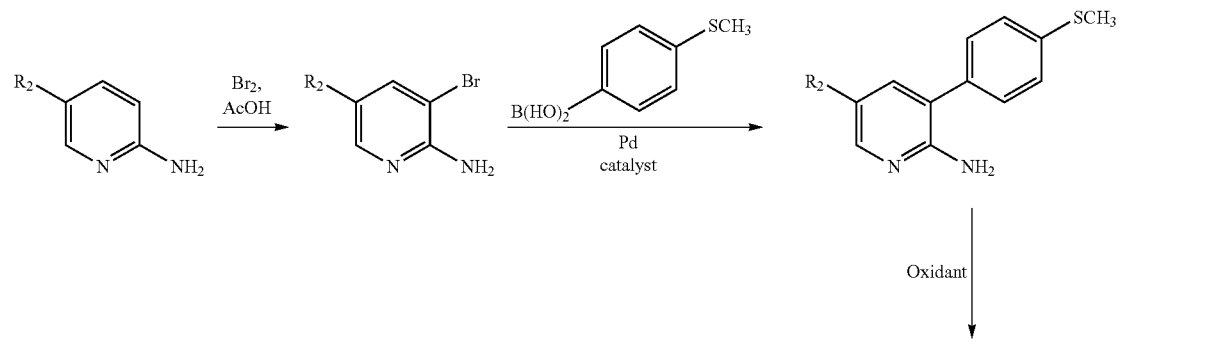

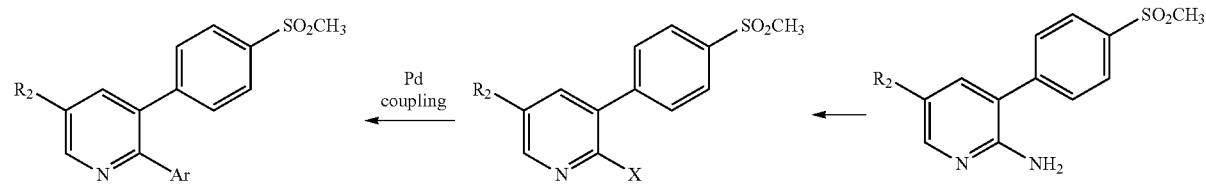

An alternate process is also disclosed in U.S. Pat. No. 5,861,419 as depicted in the following scheme.

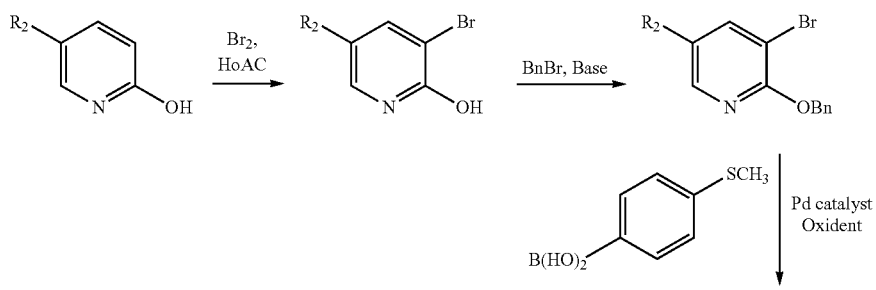

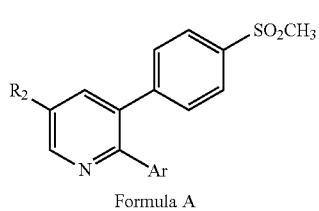 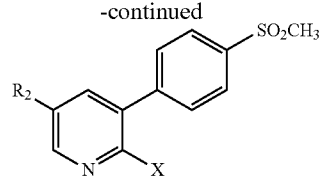 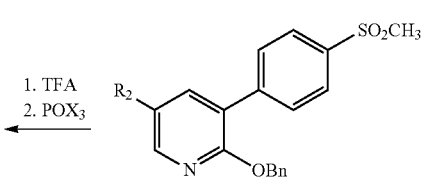

The processes described in U.S. Pat. No. 5,861,419 comprise multi-step synthesis resulting in poor yield of the final product.

U.S. Pat. No. 6,040,319 describes another process for the preparation of Etoricoxib according to the scheme below. It relates to condensation between a compound of Formula-II and a compound of Formula-IIIa, wherein X may be selected from phosphates, sulfates, acetates, perchlorate, borates, benzoate, napsylate, particularly, hexafluorophosphate, sulfate, mesylate, tosylate, triflate, acetate, trifluoroacetate, tetrafluoroborate, tetraphenyl borate, hexafluoroantimonate, chloride, bromide, fluoride, iodide, benzolate and napsylate. Sodium or potassium hydroxides, cesium carbonate, alkoxides, amides and hydrides of lithium, sodium and potassium depicted as suitable bases.

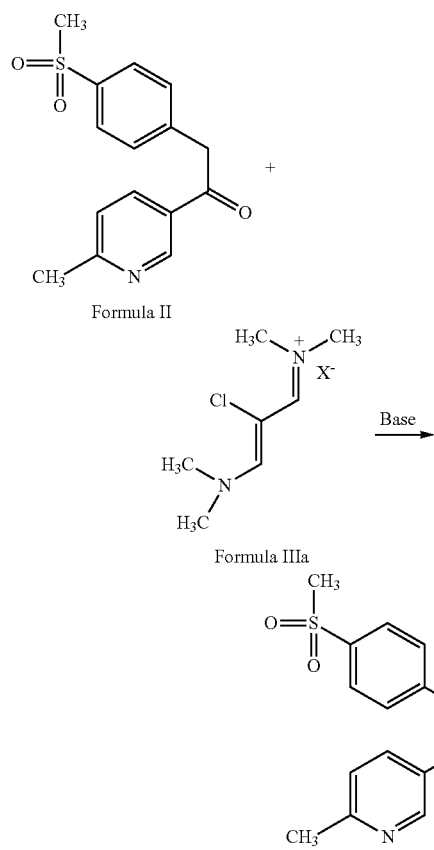

WO 99/55830 describes a process for preparing cox-2 inhibitors including etoricoxib. It involves condensation between a vinamidinium salt and a substituted benzyl pyridyl ketone derivative, which in turn is made by employing a Grignard reaction between a pyridyl amide derivative and a thiomethyl benzyl halide, followed by oxidation.

U.S. Pat. No. 6,071,936 includes substituted pyridine derivatives, their pharmaceutical compositions and a method of treating cox-2 mediated diseases. Various compounds included therein are structurally 2,3-diarylpyridine derivatives having a sulphone substitution. The synthetic scheme comprised of a palladium catalyzed diaryl coupling between a halogenated 2-aminopyridine derivative and a 4-(methylthio)phenylboronic acid followed by oxidation and further coupling with another aryl moiety.

U.S. Pat. No. 6,001,843, U.S. Pat. No. 6,596,736 B2 and U.S. Pat. No. 6,812,346 B2 also discloses structurally similar substituted pyridine derivatives and synthetic methodology applied. Their use in preparation of pharmaceutical formulations as cox-2 inhibitors is also presented in these inventions.

The patent document WO2010/097802 A2 describes a process for preparing the drug substance etoricoxib. While use of certain substituted β-chloro vinamidinium salts has been reported earlier, this invention relates to preparation of alternative β-chloro vinamidinium salts containing a cyclic or a heterocyclic substitute group. It also describes a process for preparing these alternative vinamidinium salts, as well method of purification. Polymorphic characteristics of one of such modified β-chloro vinamidinium salts viz. 2-chloro-1, 3-(bispiperidyl)trimethinium hexafluorophosphate which exists as form-I and form-II are also documented in the patent. Preparation process for etoricoxib by using such vinamidinium salts containing cyclic moieties is also described.

Nevertheless, there always exists a need to work out a newer synthetic approach that may lead to an improved and cost effective process for preparation of the said drug substance.

OBJECTS OF THE INVENTION

Therefore, it is an object of the present invention to provide a simple and effective process for a potent drug substance namely 5-Chloro-3-(4-methylsulphonyl)phenyl-2-(2-methyl-5-pyridinyl)pyridine of Formula-I, a known cyclooxygenase-2 inhibitor of established efficacy.

It is another object of this invention to provide a simple and effective process for a key intermediate of Formula-II, viz. 1-(6-methyl-3-pyridinyl)-2-[4-(methylsulphonyl)phenyl] ethanone useful in the preparation of 5-Chloro-3-(4-methylsulphonyl)phenyl-2-(2-methyl-5-pyridinyl)pyridine the drug substance structurally represented by Formula-I.

Another object of the present invention is to prepare a novel intermediate 5-Chloro-3-(4-methylthio)phenyl-2-(2-methyl-5-pyridinyl)pyridine which is structurally represented by Formula-IV, another key substance for preparation of 5-chloro-3-(4-methylsulphonyl)phenyl-2-(2-methyl-5-pyridinyl) pyridine of Formula-I.

Yet another object of this invention relates to a process for preparing the compound of Formula-IV, which is a novel intermediate in preparation of the drug substance of Formula-I.

SUMMARY OF INVENTION

In accordance with the present invention there is provided a process for synthesis of cycloxygenase-2-inhibitor etoricoxib of formula-(I) from compound of formula (IV) comprising subjecting compound of formula (IV) to oxidation in presence of oxidation catalyst and phase transfer catalyst.

In an aspect, the present invention provides a novel compound of formula (IV);

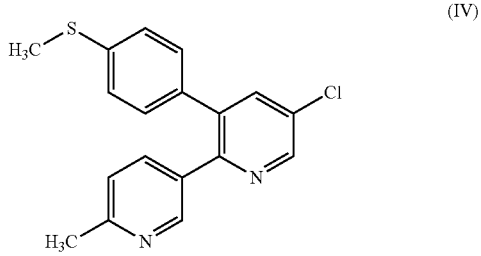 [SMILES: CSc1ccc(-c2cc(Cl)cnc2-c2ccc(C)nc2)cc1]

(IV)

In another aspect, the invention provides a process for the preparation of compound of formula (IV) comprising a reaction between a benzyl pyridyl ketone derivative of formula-(V) and a vinamidinium salt derivative of formula-(III) in presence of a base. The product mass is next subjected to a series of chemical and operational stages to obtain an annulated pyridine intermediate represented by compound of formula-(IV).

Another aspect of the invention is to provide an improved process for the preparation of etoricoxib from 4-methyl thio benzyl cyanide as a starting compound. The said compound is condensed with methyl 6-methyl nicotinate in presence of base to obtain compound (VI) which is hydrolyzed and decarboxylated to form (V). Compound (V) is condensed with vinamidinium salt derivative of formula-(III) in presence of a base. The product mass is next subjected to a series of chemical and operational stages to obtain an annulated pyridine intermediate represented by compound of formula-(IV) which when subjected to oxidation gives the desired compound, etoricoxib.

BRIEF DESCRIPTION OF THE DRAWINGS

The present invention will be described in detail with reference to the accompanying drawings. In the accompanying drawings.

DETAIL DESCRIPTION OF THE INVENTION

Figure 1:
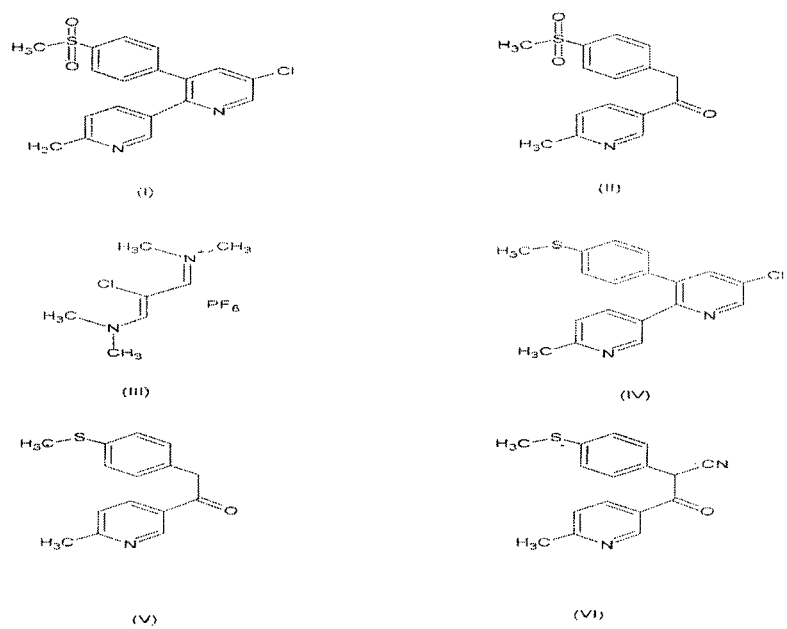
FIG. 1 illustrates the Structure Sheet
Figure 2:
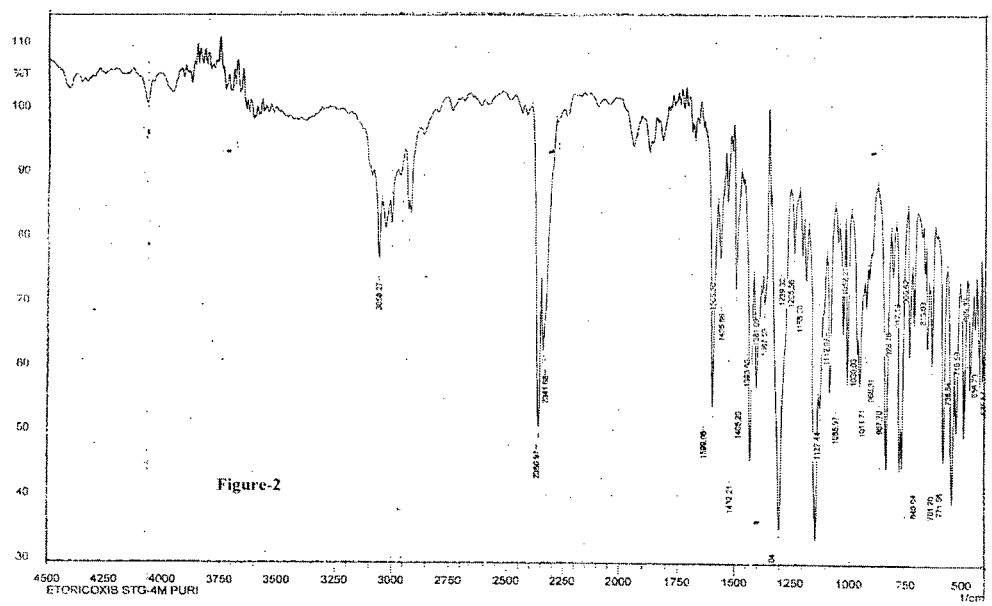
FIG. 2 illustrates the infrared spectrum of the compound of formula-(I) 5-Chloro-3-(4-methylsulphonyl)phenyl-2-(2-methyl-5-pyridinyl)pyridine i.e. etoricoxib.
Figure 3:
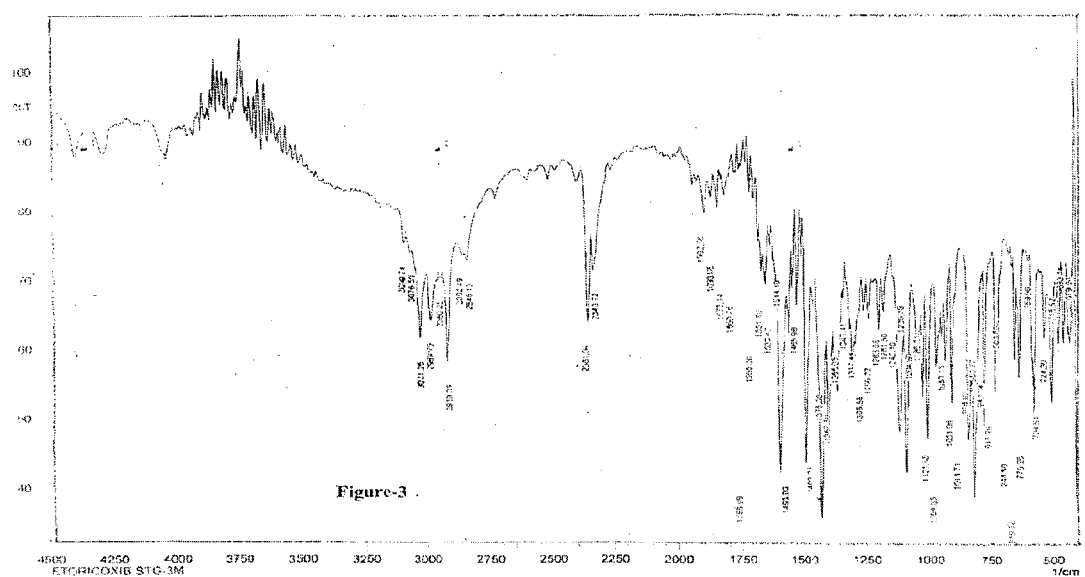
FIG. 3 illustrates the infrared spectrum of the intermediate compound of formula-(IV) i.e. 5-Chloro-3-(4-methylthio) phenyl-2-(2-methyl-5-pyridinyl)pyridine.
Figure 4:
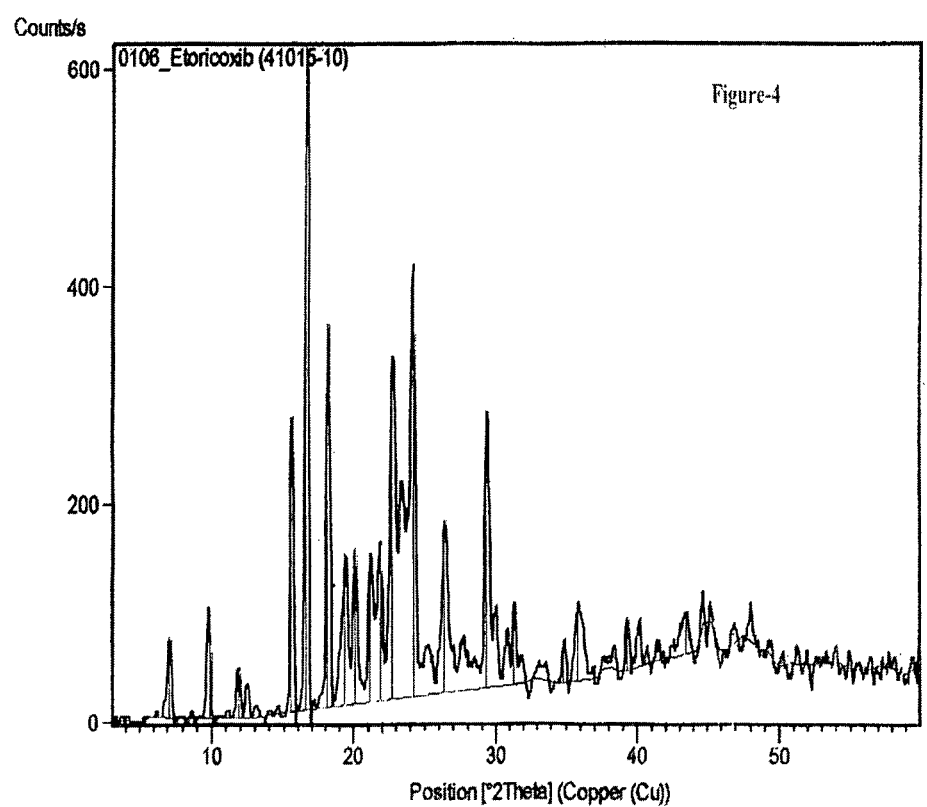
FIG. 4 illustrates the PXRD spectrum of 5-Chloro-3-(4-methylsulphonyl)phenyl-2-(2-methyl-5-pyridinyl)pyridine i.e. etoricoxib.

The invention will now be described in detail in connection with certain preferred and optional embodiments, so that various aspects thereof may be fully understood and appreciated.

The present invention, in accordance with the object of invention mentioned earlier, is described in detail in the following embodiments.

In a preferred embodiment, the present invention provides a process for the preparation of etoricoxib from compound 5-Chloro-3-(4-methylthio)phenyl-2-(2-methyl-5-pyridinyl) pyridine (IV), comprising subjecting said compound of formula (IV) to oxidation in presence of oxidation catalyst and phase transfer catalyst to obtain etoricoxib of formula-(I).

Accordingly, compound of formula (IV) 5-chloro-3-(4-methylthio)phenyl-2-(2-methyl-5-pyridinyl)pyridine is subjected to oxidation in presence of oxidizing agent selected from hydrogen peroxide, sodium peroxide etc under catalytic and biphasic condition involving organic and aqueous phases.

The biphasic mass typically comprises water, chlorinated hydrocarbon, an oxidizing agent, an oxidation catalyst and a phase transfer catalyst. Typically, the chlorinated hydrocarbon solvent is at least one solvent selected from a group of chlorinated hydrocarbons solvents consisting of such as chloroform, dichloroethane, dichloromethane and carbon tetrachloride. Typically the oxidation catalyst is at least one selected from a group of salts consisting of sodium molybdate, sodium vanadate and sodium tungstate. Typically, the phase transfer catalyst is at least one selected from a group of such catalysts consisting of methyl-tri-n-octyl ammonium chloride, methyl-tri-n-butyl ammonium chloride, methyl-tri-n-butyl ammonium chloride, benzethonium chloride, and methyl benzethonium chloride. The oxidation reaction is carried out by hydrogen peroxide aqueous solution in temperature range of 0°-20° C., Preferably, at 10°-14° C., followed by increase in temperature to achieve ambient condition while monitoring the reaction by TLC to its completion. The phases are separated, aqueous portion is extracted by the same organic solvent used in the reaction, all the organic solutions are mixed, washed with aqueous sodium carbonate solution and water till near neutral pH, dried over anhydrous sodium sulphate, optionally purified with active carbon, filtered and concentrated to remove solvent in vacuo. The residual mass is treated with an alcoholic solvent typically at least one selected from a group consisting of methanol, rectified spirit, isopropanol, n-propanol and n-butanol containing 0%-4% water v/v basis. The product mass is cooled to (−)2°-2° C., filtered, washed with the same cold solvent and dried to obtained the crude product etoricoxib of formula-(I)

Purification of crude etoricoxib so obtained involves a process of crystallization. The crude etoricoxib of formula-(I) is purified using crystallization which includes dissolving the product is dissolved in at least one alcoholic solvent typically selected from a group consisting of n-propanol iso propanol, methanol rectified spirit acetone which contains 0%-6% water v/v basis. Crude product is dissolved in the solvent at elevated temperature, treated with active carbon for a period of 15-30 minutes, filtered, and cooled to ambient temperature and further to 12°-15° C. for about an hour. The solidified product filtration is isolated, by washed with cooled solvent and dried.

Alternatively, crude etoricoxib of formula-(I) may be purified by converting to its salt. Accordingly, the process involves reacting paratoluene sulphonic acid with etoricoxib in presence of an organic solvent to obtain the salt of etoricoxib and isolating the salt substance.

Isolated etoricoxib paratoluene sulphonic acid salt is then dissolved in water under ambient condition and treated with aqueous sodium carbonate solution till it is mildly basic. The product mass is next treated with toluene at elevated temperature to extract product mass in toluene. Aqueous layer is extracted in toluene and mixed with the first toluene solution. Combined toluene solution is then washed with water, purified by treatment with active carbon, dried over anhydrous sodium sulphate, filtered and concentrated under reduced pressure to obtain a residue. The residue is re-dissolved in at least one alcoholic solvent typically selected from a group consisting of methanol, ethanol, rectified spirit, isopropanol and n-propanol, containing 0%-6% water. The solution is cooled to 5°-10° C. for a period of 1-2 hrs, filtered, washed with cooled solvent and dried to obtain purified etoricoxib.

The present invention provides a novel intermediate of formula (IV);

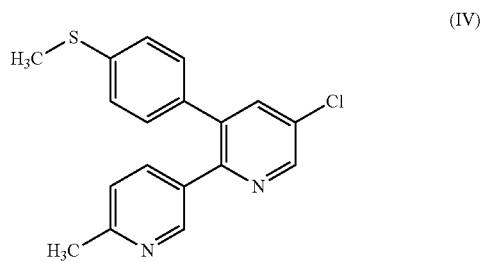 [SMILES: CSc1ccc(-c2cc(Cl)cnc2-c2ccc(C)nc2)cc1]

(IV)

In yet another embodiment, the present invention provides a process for the preparation of novel intermediate (IV), comprising reacting 1-(6-methyl-3-pyridinyl)-2[4-(methylthio) phenyl]ethanone (V) with 2-chloro-N,N-dimethylamino trimethinium hexafluoro phosphate (III) in presence of base followed by addition of alcohol and acid mixture at same temperature, and adding an aqueous solution of ammonia followed by addition of anhydrous ammonium salt to obtain (IV).

In yet another embodiment, the invention provides a simple and effective process for preparation of the compound of formula-(I) namely 5-chloro-3-(4-methylsulphonyl)phenyl-2-(2-methyl-5-pyridinyl)pyridine (etoricoxib) with high purity. The said process comprises the following steps:

a. Condensing 4-methylthio-benzylcyanide and methyl-6-methylnicotinate in presence of suitable base and suitable solvent at reflux temperature to obtain 1-(6-methyl-3-pyridinyl)-2-cyano-2-[(4-methylthio)phenyl] ethanone (VI);

b. Hydrolyzing compound (VI) of step (a) in presence of acid at 40-50 C followed by decarboxylating in situ at reflux temperature to obtain 1-(6-methyl-3-pyridinyl)-2 [4-(methylthio)phenyl]ethanone of formula (V);

c. Reacting compound of formula (V) with 2-chloro-N,N-dimethylamino trimethinium hexafluoro phosphate salt (III) in presence of base at a temperature in the range of 0°-10° C., followed by addition of alcohol and acid mixture at same temperature, adding an aqueous solution of ammonia and ammonium salt, heating, to obtain intermediate 5-Chloro-3-(4-methylsulphonyl)phenyl-2-(2-methyl-5-pyridinyl)pyridine(IV); and d. Subjecting compound of formula (IV) obtained in step (c) to oxidation in presence of oxidation catalyst and phase transfer catalyst in biphasic condition to obtain etoricoxib of formula-(I).

The process is given in Scheme 1 below:

Scheme 1

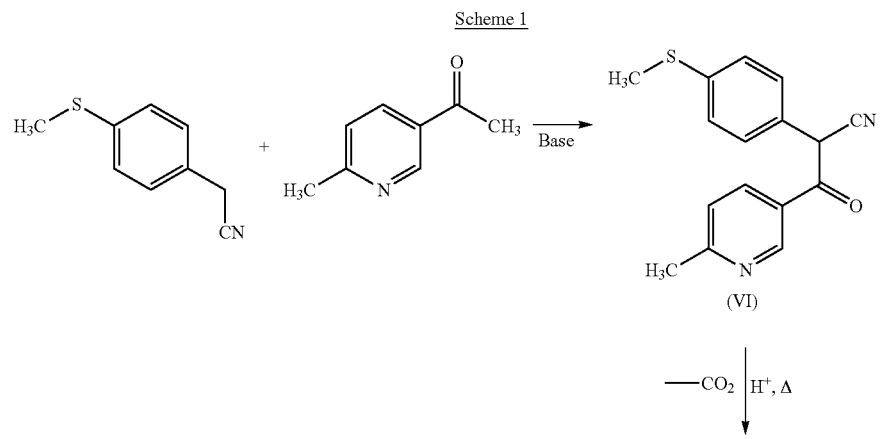

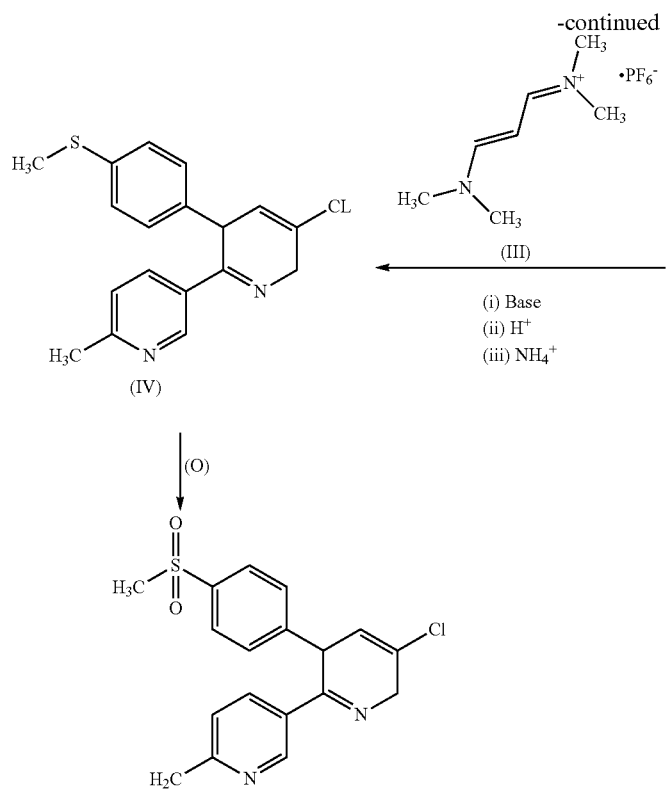
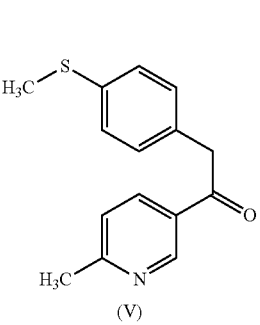

Accordingly, to the scheme 1, step (a) of the current invention involves base catalyzed condensation between 4-methylthio-benzylcyanide and methyl-6-methylnicotinate in a hydrocarbon solvent. Typically, the base is selected from a group of bases such as sodium methoxide, sodium amide, sodium hydride, potassium tert-butoxide, and potassium methoxide. Preferred base used is sodium methoxide or potassium tert-butoxide. Typically the hydrocarbons used are selected from heptane, toluene, xylene or mixtures thereof. The reaction completion is monitored by TLC analysis and the reaction mass is quenched in ice-water. pH of the mass is adjusted with a dilute acid, preferably dilute hydrochloric acid, to pH 5.0 to 6.5, preferably 5.2 to 6.3 and the product 1-(6-methyl-3-pyridinyl)-2-cyano-2-[(4-methylthio)phenyl] ethanone (VI) is isolated by filtration.

Compound of formula (VI), in step (b), is hydrolyzed in presence of acid catalyst to obtain carboxylic acid compound which on heating is decarboxylated in situ to yield 1-(6-methyl-3-pyridinyl)-2[4-(methylthio)phenyl]ethanone of formula (V). The reaction medium consists of a mixture of an organic carboxylic acid selected from a group of acids such as formic acid, glacial acetic acid, propionic acid, butyric acid, pentanoic acid, and a mineral acid such as concentrated hydrochloric acid or concentrated sulphuric acid. Typically, a combination of glacial acetic acid and concentrated hydrochloric acid is used in the process.

The compound of formula (V) of step (b) is extracted with a hydrocarbon solvent selected from a group of solvents such as hexane, heptane, cyclohexane, and toluene and further basified to pH 6.8 to 7.3 with aqueous ammonia solution. preferably, the solvent used in extraction is hexane and preferred pH range is 6.9 to 7.2. The product mass is isolated by filtration and dried at 45-60° C.

The extraction process of compound of formula (V) (step b) may optionally be accomplished by extracting the reaction mass of step (b), after completion of the reaction and pH adjustment to 6.8 to 7.3, with solvents selected from halogenated hydrocarbons such as chloroform, dichloro methane, esters such as ethyl acetate or propyl acetate. Typically dichloro methane is used as a preferred solvent. The intermediate compound (V) is isolated by concentration to remove the solvent and followed by addition of another solvent selected from lower alcohols, preferably, isopropanol, cooling the mass to 10°-12° C., filtering the product and subsequently drying at 45°-50° C.

Intermediate compound (V) obtained as above may optionally be purified by recrystallizing it form methanol.

1-(6-methyl-3-pyridinyl)-2[4-(methylsulphonyl)phenyl] ethanone compound of formula (V) according to step (c) is treated with a base catalyst in an organic solvent at a temperature range of 0°-20° C., preferably at 0°-10° C.; more preferably at 5°-8° C. The base catalyst is selected from a group consisting of sodium methoxide, potassium methoxide, potassium tert-butoxide, sodium amide and sodium hydride. Typically, the base catalyst used is potassium tert-butoxide. The organic solvent is selected from a group of tert-butanol, isopropanol, tetrahydrofuran and methyl-tert-butyl ether. Typically, the solvent used is isopropanol. The reaction mass is then reacted with the intermediate 2-chloro-N,N-dimethylamino trimethinium hexafluoro phosphate salt, the compound of formula (III) in the temperature range of 0°-10° C. for a period of 2.0-4.0 hrs, while the reaction progress is monitored by TLC until one of the reacting intermediates viz. compound of formula (V) is practically totally consumed. The reaction mass is next treated with a mixture of an alcohol solvent selected from a group consisting of methanol, ethanol, isopropanol, tert-butanol and n-propanol; and a carboxylic acid selected from a group of acids consisting of formic acid, acetic acid, n-propionic acid and n-butyric acid. Typically, the alcohol solvent used is isopropanol and the carboxylic acid used is acetic acid. The reaction mass is maintained at 0°-10° C., preferably at 5°-10° C. for 2.5 to 3.0 hrs. It is next added with an aqueous solution of ammonia followed by addition of ammonium salt selected from a group of salts including ammonium acetate, ammonium carbonate etc. Typically, ammonium acetate is used in the reaction. The mass is refluxed to complete the reaction, cooled to room temperature followed by addition of ammonia solution and formaldehyde solution. The reaction solvent is removed by distillation at reduced pressure, adding another solvent toluene, re-heating the reaction mass to 60°-65° C. The organic and aqueous layers are separated. Aqueous layer is washed with toluene, combined toluene layers are washed with aqueous sodium carbonate solution followed by water, treated with active carbon, filtered, dried over anhydrous sodium sulphate and concentrated under vacuum to remove the solvent. To the residual mass is added alcoholic solvent selected from a group of methanol, isopropanol, rectified spirit, n-propanol or a mixture thereof. Typically, isopropanol is utilized for addition, followed by cooling to solidify the product. The product mass is filtered, washed with isopropanol and dried to obtain compound of formula (IV).

Compound of formula (IV) is crystallized from an organic solvent selected from a group of alcoholic solvents including ethyl alcohol, rectified spirit, n-propanol, isopropanol or a mixture thereof, which contain 0-6% water v/v basis. Compound of formula (IV) is dissolved in an adequate quantity of the solvent, refluxed to dissolve, filtered, cooled to solidify the product and filtered to isolate the product. Typically, isopropanol is used as the solvent for purification. The product is isolated and dried under at 45°-50° C.

compound of formula (IV) 5-chloro-3-(4-methylthio)phenyl-2-(2-methyl-5-pyridinyl)pyridine is subjected to oxidation in presence of oxidizing agent selected from hydrogen peroxide, sodium peroxide etc under catalytic and biphasic condition involving organic and aqueous phases.

The biphasic mass typically comprises water, chlorinated hydrocarbon, an oxidizing agent, an oxidation catalyst and a phase transfer catalyst. Typically, the chlorinated hydrocarbon solvent is at least one solvent selected from a group of chlorinated hydrocarbons solvents consisting of such as chloroform, dichloroethane, dichloromethane and carbon tetrachloride. Typically, the oxidation catalyst is at least one selected from a group of salts consisting of sodium molybdate, sodium vanadate and sodium tungstate. Typically, the phase transfer catalyst is at least one selected from a group of such catalysts consisting of methyl-tri-n-octyl ammonium chloride, methyl-tri-n-butyl ammonium chloride, methyl-tri-n-butyl ammonium chloride, benzethonium chloride, and methyl benzethonium chloride. The oxidation reaction is carried out by hydrogen peroxide aqueous solution in temperature range of 0°-20° C., Preferably, at 10°-14° C., followed by increase in temperature to achieve ambient condition while monitoring the reaction by TLC to its completion. The phases are separated, aqueous portion is extracted by the same organic solvent used in the reaction, all the organic solutions are mixed, washed with aqueous sodium carbonate solution and water till near neutral pH, dried over anhydrous sodium sulphate, optionally purified with active carbon, filtered and concentrated to remove solvent in vacuo. The residual mass is treated with an alcoholic solvent typically at least one selected from a group consisting of methanol, rectified spirit, isopropanol, n-propanol and n-butanol containing 0%-4% water v/v basis. The product mass is cooled to (−)2°-2° C., filtered, washed with the same cold solvent and dried to obtained the crude product etoricoxib of formula-(I)

Purification of crude etoricoxib so obtained involves a process of crystallization. The crude etoricoxib of formula-(I) is purified using crystallization which includes dissolving the product is dissolved in at least one alcoholic solvent typically selected from a group consisting of n-propanol iso propanol, methanol rectified spirit acetone which contains 0%-6% water v/v basis. Crude product is dissolved in the solvent at elevated temperature, treated with active carbon for a period of 15-30 minutes, filtered, and cooled to ambient temperature and further to 12°-15° C. for about an hour. The solidified product filtration is isolated, by washed with cooled solvent and dried.

Alternatively, crude etoricoxib of formula-(I) may be purified by converting to its salt. Accordingly, the process involves reacting paratoluene sulphonic acid with etoricoxib in presence of an organic solvent to obtain the salt of etoricoxib and isolating the salt substance.

Isolated etoricoxib paratoluene sulphonic acid salt is then dissolved in water under ambient condition and treated with aqueous sodium carbonate solution till it is mildly basic. The product mass is next treated with toluene at elevated temperature to extract product mass in toluene. Aqueous layer is extracted in toluene and mixed with the first toluene solution. Combined toluene solution is then washed with water, purified by treatment with active carbon, dried over anhydrous sodium sulphate, filtered and concentrated under reduced pressure to obtain a residue. The residue is re-dissolved in at least one alcoholic solvent typically selected from a group consisting of methanol, ethanol, rectified spirit, isopropanol and n-propanol, containing 0%-6% water. The solution is cooled to 5°-10° C. for a period of 1-2 hrs, filtered, washed with cooled solvent and dried to obtain purified etoricoxib.

The invention provides a process for the preparation of the vinamidinium salt 2-Chloro-N,N-dimethylaminotrimethinium hexafluorophosphate represented by formula (III). Typically, N,N-dimethylformamide is related with chloroacetyl chloride at approximately 50°-55° C. followed by addition of phosphorous oxychloride at an elevated temperature of 65°-70° C. for a period of 5 to 6 hrs. It is next cooled to ambient temperature and treated with ice water mixture containing hexa fluoro phosphoric acid, added with aqueous solution of sodium hydroxide to adjust the pH to around 2.0 to 2.8, and maintained under stirring for a period approximately 30 minutes. The intermediate compound of formula (V) was isolated by filtration, washing followed by purification in aqueous isopropanol and drying. It may optionally be repurified by dissolving in methanol at elevated temperature up to reflux, treatment with active carbon, filtration of the solution, partial concentration by removal of solvent by distillation, cooling the mass to effect crystallization, filtration and drying.

In yet another embodiment, the invention provides a process for preparation of 1-(6-methyl-3-pyridinyl)-2-[(4-Methylsulphonyl)phenyl]ethanone of formula (II), comprising;

a. Condensing 4-methylthio-benzylcyanide and methyl-6-methylnicotinate in presence of suitable base and suitable solvent at reflux temperature to obtain 1-(6-methyl-3-pyridinyl)-2-cyano-2-[(4-methylthio)phenyl]ethanone (VI) wet mass;

b. Hydrolyzing the wet mass of compound (VI) of step (a) in presence of acid at 40-50° C. followed by decarboxylating in situ at reflux temperature to obtain 1-(6-methyl-3-pyridinyl)-2[4-(methylthio)phenyl]ethanone of formula (V); and c. Subjecting compound of formula (V), obtained in step (b) to oxidation in presence of oxidation catalyst and phase transfer catalyst followed by addition of alcohol and acid mixture, adding an aqueous solution of ammonia followed by addition of ammonium salt, heating to obtain (II).

According to the process, 4-Methylthiobenzyl cyanide and methyl-6-methyl nicotinate are subjected to base catalyzed condensation as described herein above. The product wet cake mass is then subjected to acid catalyzed hydrolysis and subsequent thermal decarboxylation to yield 1-(6-methyl-3-pyridinyl)-2[4-(methylsulphonyl)phenyl]ethanone, the compound of formula-(V), as per details given earlier. This intermediate compound (V), as wet product mass isolated from the reaction mass is dissolved in an organic solvent for carrying out next stage of oxidation. The solvent is selected from chlorinated hydrocarbons such as chloroform, dichloro ethane, dichloromethane and carbon tetrachloride. The oxidation catalyst is selected from a group of salts consisting of sodium molybdate, sodium vanadate and sodium tungstate. The phase transfer catalyst is at least one selected from a group of such catalysts consisting of methyl-tri-n-octyl ammonium chloride, methyl-tri-n-butyl ammonium chloride, methyl-tri-n-butyl ammonium chloride, benzethonium chloride, and methyl benzethonium chloride. The oxidation reaction is carried out in presence of peroxide such as hydrogen peroxide, sodium peroxide etc. in aqueous solution at a temperature range of 0°-20° C., preferably, at 10°-14° C., followed by increase in temperature to achieve ambient condition while monitoring the reaction by TLC to its completion. The phases are separated, aqueous portion is extracted by the same organic solvent used in the reaction, all the organic solutions are mixed, washed with aqueous sodium carbonate solution and water till near neutral pH, dried over anhydrous sodium sulphate, optionally purified with active carbon, filtered and concentrated to remove solvent in vacuo. The residual mass is treated with an alcoholic solvent at least one selected from a group consisting of methanol, rectified spirit, isopropanol, n-propanol and n-butanol containing 0%-4% water v/v basis. The product mass is cooled to (−)2°-2° C., filtered, washed with the same cold solvent and dried to obtain the crude product 1-(6-methyl-3-pyridinyl)-2-[(4-methylsulphonyl)phenyl]ethanone (II).

Alternatively, the intermediate compound of formula-(II), is prepared by a process which involves condensation between 4-methyl sulphonyl phenyl acetic acid and methyl-6-methylnicotinate in presence of an organometallic substance such as tert-butyl magnesium chloride as described in the art.

The present invention will now be illustrated by the following examples, which are not intended to limit effective scope of the claims. As a consequence, any variations of the invention described above are not to be regarded as departure from the spirit and the scope of invention as claimed. The present invention has been described in terms of its specific embodiments, and for those skilled in the art various modifications, parallels and equivalents will be apparent and are intended to be included within the scope of present invention.

Example-1

Preparation of 1-(6-methyl-3-pyridinyl)-2-Cyano-2-[(4-Methylthio)phenyl]ethanone (VI)

4-Methyl thio benzyl cyanide (10.0 gm) was dissolved is (100 ml) Toluene and reaction mass was refluxed. Methyl-6-Methyl Nicotinate (10.87 gm) was added slowly at reflux temperature within about 30 minutes. The reaction mass was stirred for 10 minutes. Sodium methoxide solution (30% w/w) 19.96 gm was charged within 30 minutes. The reaction temperature was maintained at reflux till compliance by TLC examination, till spot corresponding to methyl-6-methyl nicotinate was practically absent. The reaction mass was cooled to 25°-30° C. under stirring. Reaction mass was quenched in crushed ice (75 gm)+water (10 ml) mixture. The pH of reaction mass was adjusted between 5.2 to 6.2 with dilute hydrochloric acid. The reaction mass was stirred for an hour, filtered, washed with water and dried at 60-70° C. (Yield 16 gm, Purity 96.3% by HPLC).

Example-2

Preparation of 1-(6-methyl-3-pyridinyl)-2-Cyano-2-[(4-Methylthio)phenyl]ethanone (VI)

4-Methyl thio benzyl cyanide (10.0 gm) was dissolved is (80 ml) Toluene+20 ml n-heptane and reaction mass was refluxed. Methyl-6-Methyl Nicotinate (11.30 gm) was added slowly at reflux temperature within about 30 minutes. The reaction mass was stirred for 10 minutes. Sodium methoxide solution (30% w/w) 19.96 gm was charged within 30 mints. The reaction temperature was maintained at reflux till compliance by TLC examination, till spot corresponding to methyl-6-methyl nicotinate was practically absent. The reaction mass was cooled to 25°-30° C. under stirring. Reaction mass was quenched in crushed ice (75 gm)+water (15 ml) mixture. The pH of reaction mass was adjusted between 5.2 to 6.2 with dilute hydrochloric acid. The reaction mass was stirred for an hour, filtered, washed with water and dried at 60-70° C. temp. (yield 15.7 gm, Purity 95.7% by HPLC).

Example-3

Preparation of 1-(6-methyl-3-pyridinyl)-2-[(4-Methylthio)phenyl]ethanone (V)

1-(6-methyl-3-pyridinyl)-2-cyano-2-[(4-Methylthio)phenyl]ethanone (VI) (10 gm) was added to a mixture of concentrate Hydrochloric acid (70 ml) and Glacial acetic acid (25 ml) at 40°-50° C., followed by decarboxylation at reflux temperature. Reaction progress was monitored by TLC till completion of the reaction. Reaction mass was cooled to room temperature and was washed by extracting with hexane.

The above reaction mass was slowly poured into a mixture of (31.75 ml) concentrate ammonia solution and (10.00 ml) water. Reaction mass was stirred for 10 minutes and pH was adjusted between 6.80 to 7.20 with dilute ammonia solution at 0-5° C. The quenched mass was stirred for 30-60 minutes and filtered. The product obtained was washed with water, dried in a tray dryer at 45-50° C. till its moisture content was below 2% to give (V) as creamish yellow powder. (yield=8.8 gm, HPLC purity=93.89%)

Example-4

Preparation of 1-(6-methyl-3-pyridinyl)-2-[(4-Methylthio)phenyl]ethanone (V)

1-(6-methyl-3-pyridinyl)-2-cyano-2-[(4-Methylthio)phenyl]ethanone (VI) (10 gm) was added to a mixture of concentrate Hydrochloric acid (80 ml) and Glacial acetic acid (30 ml) at 40°-50° C., followed by decarboxylation at reflux temperature. Reaction progress was monitored by TLC till completion of the reaction. Reaction mass was cooled to room temperature and was washed by extracting with hexane. The above reaction mass was slowly poured in to mixture of (31.75 ml) concentrate ammonia solution and (10.00 ml) water. Reaction mass was stirred for 10 minutes and pH was adjusted between 7.00 to 7.20 with dilute ammonia solution at 0-5° C. The quenched mass was stirred for 30-60 minutes and filtered. The product obtained was washed with water, dried in a tray dryer at 45-50° C. till its moisture content was below 2% to give (V) as creamish yellow powder. (yield=8.70 gm, HPLC purity=95.00%)

Example-5

Preparation of 1-(6-methyl-3-pyridinyl)-2-[(4-Methylthio)phenyl]ethanone (V)

To Compound (VI) (10 gm) (prepared by a process described above in Example-4) was added to a mixture of concentrate hydrochloric acid (75 ml) and Glacial acetic acid (25 ml) at ambient temperature, heated to 70-80 C. After completion of reaction it was cooled to room temperature and extracted with (12 ml) Toluene.

The above reaction mass was further added into a mixture of (31.75 ml) ammonia solution and water 10.00 ml and stirred. Reaction mass was adjusted to pH between 6.8 to 7.2 using sodium carbonate solution (5% w/v) at 0-5° C. temperature. It was stirred for 60 minutes and filtered to obtain wet cake. Wet product was washed twice with (10 ml) water. The wet cake was dissolved in (70 ml) dichloromethane followed by addition of (20 ml) water, stirred for 10 minutes and layers were separated. Aqueous layer was extracted twice with dichloromethane. Combined organic layer containing the product was washed with (10 ml) water (10.00 ml), dried over anhydrous sodium sulphate and purified by activated carbon treatment.

Product layer was concentrated by distilling out dichloromethane at atmospheric pressure to obtain a semi-solid residue. The residue mass was degassed under vacuum for 30 minutes. Isopropyl alcohol (5 ml) was added to the mass and it was cooled to 10-12° C. After stirring for 1 hour at 10-12° C. temperature, it was filtered, and washed with chilled isopropyl alcohol (2.00 ml). The product was dried in a vacuum oven at 45°-50° C. temperature (7 gm, purity by HPLC 93.5%)

Dried product obtained (7 gm) was purified by treatment with methyl iso butyl ketone (17.5 ml). The product slurry was stirred for 30 minutes, filtered and washed with methyl iso butyl ketone (2 ml), and dried under vacuum oven at 40-45° C. temperature. The purified product (5 gm) showed HPLC purity 95.00%.

Example-6

Preparation of 1-(6-methyl-3-pyridinyl)-2-[(4-Methylthio)phenyl]ethanone (V)

To compound (VI) (10 gm) (as per process described above in Example-4) was added a mixture of concentrate hydrochloric acid (75 ml) and Glacial acetic acid (25 ml) After completion of reaction it was cooled to room temperature and extracted with (12 ml) Toluene.

The above reaction mass was added in to a mixture of (31.75 ml) ammonia solution and water (10.00 ml) and stirred. Reaction mass was adjusted to pH between 6.9 to 7.1 using sodium carbonate solution (5% w/v) at 0-5° C. temperature. It was stirred for 60 minutes and filtered to obtain wet cake. Wet product was washed twice with (10 ml) water. Product wet cake was dissolved in (70 ml) dichloromethane followed by addition of (20 ml) water, stirred for 10 minutes and layers were separated. Aqueous layer was extracted twice with dichloromethane. Combined organic layer containing the product was washed with water (10.00 ml), dried over anhydrous sodium sulphate and purified by activated carbon treatment.

Product layer was concentrated by distilling out dichloromethane at atmospheric pressure to obtain a semi-solid residue. The residue mass was degassed under vacuum for 30 minutes. Isopropyl alcohol (7.5 ml) was added to the mass and it was cooled to 8-10° C. temperature. After stirring for 1 hour at 8-10° C. temperature, it was filtered, and washed with chilled isopropyl alcohol (2.00 ml). The product was dried in a vacuum oven at 45°-50° C. to give dried product (7 gm, purity by HPLC 93.24%)

Dried product obtained (7 gm) was purified by treatment with methyl iso butyl ketone (17.5 ml). The product slurry was stirred for 30 minutes, filtered and washed with methyl iso butyl ketone (2 ml), and dried under vacuum oven at 40-45° C. temperature. The purified product (5.2 gm) showed HPLC purity 95.40%.

Example-7

Purification of 1-(6-methyl-3-pyridinyl)-2-[(4-methylthio)phenyl]Ethanone (V)

The dried product 1-(6-methyl-3-pyridinyl)-2-[(4-Methylthio)phenyl]ethanone (V) (10 gms) and methanol (150 ml) were heated till dissolved. Activated carbon (0.5 gm) was added, the reaction mass was maintained under stirring for 30 minutes, and then filtered. Filtrate was cooled under stirring at 0°-3° C. for an hour, the product mass was filtered and washed with chilled methanol (2.5 ml). Purified product obtained thus was dried under vacuum at 45°-50° C. (yield 4.5 gm, HPLC purity 98.65%.)

Example-8

Purification of 1-(6-methyl-3-pyridinyl)-2-[(4-methylthio)phenyl]Ethanone (V)

The dried product 1-(6-methyl-3-pyridinyl)-2-[(4-Methylthio)phenyl]ethanone (V) (10 gms) and methanol (98 ml)+(2 ml) water were heated till dissolved. Activated carbon (0.5 gm) was added, the reaction mass was maintained under stirring for 30 minutes, and then filtered. Filtrate was cooled under stirring at 0°-3° C. for an hour, the product mass was filtered and washed with chilled methanol (2.5 ml). Purified product obtained thus was dried under vacuum at 45°-50° C. (yield 5.5 gm, HPLC purity 98.22%)

Example-9

Preparation of vinamidinium salt 2-chloro-N,N-dimethyl amino trimethinium hexafluoro phosphate (III)

N,N-Dimethyl formamide (440 ml) was heated to 50°-55° C. and chloro acetyl chloride (99 gms) was slowly added over a period of 3-4 hrs. Reaction mass was heated further to 65°-70° C. and phosphorous oxychloride (140 gm) was gradually added in about 5-6 hrs. The mass was maintained under stirring for 5 hrs at 65-70° C., cooled to 25°-30° C. followed by addition into crushed ice and water containing hexafluoro phosphoric acid (232 gms) and sodium hydroxide while maintaining the pH around 2.0 to 2.2. Quenched mass was stirred for 30 minutes, filtered to isolate solid product and washed with cold water (yield of wet product 260-300 gms)

Vinamidium chloride salt (III) obtained as above was purified by treatment with aqueous isopropyl alcohol at 75°-80° C., followed by cooling to 20°-23° C. The product slurry mass was filtered, washed with isopropyl alcohol and dried at 55°-65° C. till its moisture content was below 0.5% (yield 174 gms) m.p. 124-127° C.

Example-10

Preparation of vinamidinium salt 2-chloro-N,N-dimethyl amino trimethinium hexafluoro phosphate (III)

N,N-Dimethyl formamide (400 ml) was heated to 50°-55° C. and chloro acetyl chloride (99 gms) was slowly added over a period of 3-4 hrs. Reaction mass was heated further to 65°-70° C. and phosphorous oxychloride (132 gm) was gradually added in about 5-6 hrs. The mass was maintained under stirring for 5 hrs at 65-70° C., cooled to 25°-30° C. followed by slow addition into crushed ice and water containing hexafluoro phosphoric acid (232 gms) and sodium hydroxide while maintaining the pH around 2.1 to 2.5. Quenched mass was stirred for 30 minutes, filtered to isolate solid product and washed with cold water (yield of wet product 260-300 gms)

Vinamidium chloride salt (III) obtained as above was purified by treatment with aqueous isopropyl alcohol at 75°-80° C., followed by cooling to 20°-23° C. The product slurry mass was filtered, washed with isopropyl alcohol and dried at 55°-65° C. till its moisture content was below 0.5% (yield 165 gms). m.p. 124-127° C.

Example-11

Purification of 2-chloro-N,N-dimethyl amino trimethinium hexafluoro phosphate (III)

Compound (III) as obtained above in example 10 was purified by crystallization from methanol. The material (10 gms) was added with methanol (150 ml) and heated to reflux temperature. The mass was treated with active carbon (0.5 gms) for 30 minutes, filtered hot, and then concentrated by distillation of 60-70 ml methanol. The concentrated material was next gradually cooled to room temperature and then to 2°-5° C. Purified product was filtered and washed with cold methanol (5 ml). It was dried at 50°-60° C., till constant weight (yield 8.2 gms HPLC purity 98.80%)

Example-12

Purification of 2-chloro-N,N-dimethyl amino trimethinium hexafluoro phosphate (III)

Compound (III) as obtained above in example 10 was purified by crystallization from methanol. The material (10 gms) was added with methanol (125 ml) and heated to reflux temperature. The mass was treated with active carbon (0.5 gms) for 30 minutes, filtered hot, concentrated by distillation of 60-70 ml methanol. The concentrated material was gradually cooled to room temperature and further cooled to 2°-5° C. Purified product was filtered and washed with cold methanol (5 ml). It was dried at 50°-60° C., till constant weight (yield 8.5 gms, HPLC purity 98.95%)

Example-13

Purification of 2-chloro-N,N-dimethyl amino trimethinium hexafluoro phosphate (III)

Compound (III) as obtained above in example 10 was purified by crystallization from methanol. The material (10 gms) was added with methanol (200 ml) and heated to reflux temperature. The mass was treated with active carbon (0.5 gms) for 30 minutes, filtered hot, concentrated by distillation of 60-70 ml methanol. The concentrated material was t gradually cooled to room temperature and further cooled to 2°-5° C. Purified product was filtered and washed with cold methanol (5 ml). It was dried in tray drier at 50°-60° C. till constant weight (yield 7.2 gms, HPLC purity 99.14%)

Example-14

Preparation of 5-chloro-3-(4-methylthio)phenyl-2-(2-Methyl-5-pyridinyl)pyridine-(IV)

1-(6-methyl-3-pyridinyl)-2[4-(methylthio)phenyl]ethanone, compound of formula (V) (10 gms) and isopropanol (150 ml) were slurried and maintained at 5°-8° C. for 20-30 minutes. Potassium tert-butoxide powder (5.01 gms) was gradually added to the reaction mixture while maintaining the reaction mass at 5°-8° C. over a period of half an hour. The reaction mass was maintained at the same temperature for 3 hrs under stirring. 2, Chloro-N,N-dimethylamino trimethinium hexafluoro phosphate salt (III, 13 gms) was added to the reaction mixture while maintaining the reaction mass at 5°-8° C. The reaction was continued for 2.5 to 4.0 hrs till completed as per TLC monitoring with regard to absence of parent compound of formula (V).

Above reaction mass was added in approximately 15-30 minutes into a mixture of isopropanol (13.0 ml) and glacial acetic acid (15 ml) maintained at 5°-10° C. It was further stirred for 2.5 to 3.0 hrs. Ammonia solution (27 ml) was then added to it and mass was stirred for 10 minutes. Anhydrous ammonium acetate (2.4 gms) was then added and reaction mass was heated slowly to reflux temperature for a period of 5-6 hrs. Formation of the desired product and reaction completion was monitored by TLC analysis. Reaction mass was cooled to ambient temperature and additional quantity ammonia solution (27 ml) was again added followed by formaldehyde solution (0.85 ml) Isopropanol was removed from the reaction mass at 45°-55° C. under vacuum. Toluene (80 ml) was added, reaction mass was again heated to 60°-65° C. for 30 minutes, allowed to settle and then organic and aqueous layers were separated. Aqueous layer was re-extracted with toluene (40 ml×2), toluene extracts mixed, washed with 10% sodium carbonate solution (60 ml) and water (60 ml). It was next treated with active carbon (1.0 gm) dried over anhydrous sodium sulphate, filtered and concentrated to remove solvent at 55°-60° C. under vacuum. Isopropanol (35 ml) was added to residual mass and it was cooled gradually to 0°-3° C. for 1-2 hours. Product mass was filtered, washed with 3-5 ml cold isopropanol, and dried at 60°-70° to obtain (I). (yield 7.3 gms, m.p. 98°-102° C., purity by HPLC 97.60%)

Example-15

Preparation of 5-chloro-3-(4-methylthio)phenyl-2-(2-Methyl-5-pyridinyl)pyridine-(IV)

1-(6-methyl-3-pyridinyl)-2-[4-(methylthio)phenyl]ethanone, compound of formula (V) (10 gms) and isopropanol (150 ml) were slurried and maintained at 5°-8° C. for 20-30 minutes. Potassium methoxide powder (2.91 gms) was gradually added to the reaction mixture while maintaining the reaction mass at 5°-8° C. over a period of half an hour. The reaction mass was maintained at the same temperature for 3 hrs under stirring. 2, Chloro-N,N-dimethylamino trimethinium hexafluoro phosphate salt (III, 12.6 gms) was added to the reaction mixture while maintaining the reaction mass at 5°-8° C. The reaction was continued for 2.5 to 4.0 hrs till completed as per TLC monitoring with regard to absence of parent compound of formula (V).

Above reaction mass was added in approximately 15-30 minutes into a mixture of isopropanol (13.0 ml) and glacial acetic acid (14.4 ml) maintained at 5°-10° C. It was further stirred for 2.5 to 3.0 hrs. Ammonia solution (27 ml) was then added to it and mass was stirred for 10 minutes. Anhydrous ammonium acetate (2.4 gms) was then added and reaction mass was heated slowly to reflux temperature for a period of 5-6 hrs. Formation of the desired product and reaction completion was monitored by TLC analysis. Reaction mass was cooled to ambient temperature and additional quantity ammonia solution (27 ml) was again added followed by formaldehyde solution (0.9 ml) Isopropanol was removed from the reaction mass at 45°-55° C. under vacuum. Toluene (80 ml) was added, reaction mass was again heated to 60°-65° C. for 30 minutes, allowed to settle and then organic and aqueous layers were separated. Aqueous layer was re-extracted with toluene (40 ml×2), toluene extracts mixed, washed with 10% sodium carbonate solution (60 ml) and water (60 ml). It was next treated with active carbon (1.0 gm) dried over anhydrous sodium sulphate, filtered and concentrated to remove solvent at 55°-60° C. under vacuum. Isopropanol (35 ml) was added to residual mass and it was cooled gradually to 0°-3° C. for 1-2 hours. Product mass was filtered, washed with 3-5 ml cold isopropanol, and dried at 60°-70° C. to obtain (I). (yield 7.0 gms, m.p. 98°-102° C., purity by HPLC 97.34%)

Example-16

Purification of 5-Chloro-3-(4-methylthio)phenyl-2-(2-methyl-5-pyridinyl)pyridine (IV)

Compound (IV) as obtained above (18 gm) was dissolved in isopropanol (54 ml) at 60°-65° C. under stirring. The solution was filtered hot and filtrate was cooled gradually to ambient temperature first and then to 0°-5° C. The product slurry was maintained under cooling for 2.0 hrs, filtered, washed with chilled (5-10 ml) isopropanol dried at 45°-50° (yield 15.5 gms, m.p. 103°-106° C., HPLC purity=98.6%).

Example-17

Purification of 5-Chloro-3-(4-methylthio)phenyl-2-(2-methyl-5-pyridinyl)pyridine (IV)

Compound (IV) as obtained above (18 gm) was dissolved in mixture of isopropanol (45 ml)+water (0.90 ml) at 60°-65° C. under stirring. The solution was filtered hot and filtrate was cooled gradually to ambient temperature first and then to 0°-5° C. The product slurry was maintained under cooling for 2.0 hrs, filtered, washed with chilled (5-10 ml) isopropanol and dried at 45°-50° (yield 16 gms, m.p 103°-107° C., HPLC purity=98.8%)

Example-18

Purification of 5-Chloro-3-(4-methylthio)phenyl-2-(2-methyl-5-pyridinyl)pyridine (IV)

Compound (IV) as obtained above (18 gm) was dissolved in isopropanol (90 ml)+water (3.60 ml) at 60°-65° C. under stirring. The solution was filtered hot and filtrate was cooled gradually to ambient temperature first and then to 0°-5° C. The product slurry was maintained under cooling for 2.0 hrs, filtered, washed with chilled (5-10 ml) isopropanol and dried at 60°-70° (yield 14 gms, m.p. 102°-105° C., HPLC purity=98.2%)

Example-19

Preparation of 5-Chloro-3-(4-methylsulphonyl)phenyl-2-(2-methyl-5-pyridyl)pyridine(I)

Compound of formula (IV) viz. 5-chloro-3-(4-methylthio) phenyl-2-(2-methyl-5-pyridyl)-pyridine (10 gms) was dissolved in dichloromethane (100 ml) and stirred at 25°-28° C. Sulphuric acid (0.94 gms) dissolved in water (0.5 ml) was added slowly to the above solution at 10°-15° C. A solution of sodium tungstate (0.17 gms) in water (1.5 ml) was then added gradually to it, followed by further addition of methyl-tri-n-octylammonium chloride (0.25 gms) and dichloromethane (2 ml). The reaction mass was then subjected to oxidation by gradual addition of 50% hydrogen peroxide solution (6.87 gms) in water (2 ml), while maintaining the reaction temperature at 8-10° C. over a period of approximately 1.5 to 2.0 hrs. The reaction temperature was gradually raised to 28°-30° C. and maintained for several hours while monitoring by TLC till reaction completion. Reaction mass was added with water (50 ml), and 10% sodium bicarbonate solution to maintain pH at 6.8-7.0. Dichloromethane layer containing product was separated and aqueous mass was extracted twice with dichloromethane (25 ml). Dichloromethane layers were mixed, washed twice with water (20 ml), dried over anhydrous sodium sulphate and treated with active carbon (0.8 gms). Filtered product solution was concentrated by distillation to obtained product residue. Solvent traces were removed by vacuum application and isopropanol (30 ml) was added. The mass was cooled to (−)2°-2° C. for a period of 2 hrs. Product was isolated by filtration, washed with cooled IPA (3 ml) followed by drying at 60°-70° C. (yield 7.2 gms, m.p. 129°-131° C. HPLC purity=97.14%, light creamish colored powder).

Example-20

Preparation of 5-Chloro-3-(4-methylsulphonyl)phenyl-2-(2-methyl-5-pyridyl)pyridine (I)

Compound of formula (IV) viz. 5-chloro-3-(4-methylthio) phenyl-2-(2-methyl-5-pyridyl)-pyridine (10 gms) was dissolved in dichloromethane (100 ml) and stirred at 25°-28° C. Sulphuric acid (0.94 gms) dissolved in water (0.5 ml) was added slowly to the above solution at 10°-15° C. A solution of sodium tungstate (0.17 gms) in water (1.5 ml) was then added gradually to it, followed by further addition of methyl-tri-n-octylammonium chloride (0.25 gms) and dichloromethane (2 ml). The reaction mass was then subjected to oxidation by gradual addition of 50% hydrogen peroxide solution (5.62 gms) in water (2 ml), while maintaining the reaction temperature at 10-12° C. over a period of approximately 1.5 to 2.0 hrs. The reaction temperature was gradually raised to 28°-30° C. and maintained for several hours while monitoring by TLC till reaction completion. Reaction mass was added with water (50 ml), and 10% sodium bicarbonate solution to maintain pH at 6.6-6.8. Dichloromethane layer containing product was separated and aqueous mass was extracted twice with dichloromethane (25 ml). Dichloromethane layers were mixed, washed twice with water (20 ml), dried over anhydrous sodium sulphate and treated with active carbon (0.8 gms). Filtered product solution was concentrated by distillation to obtained product residue. Solvent traces were removed by vacuum application and isopropanol (30 ml) was added. The mass was cooled to (−)2°-2° C. for a period of 2 hrs. Product was isolated by filtration, washed with cooled IPA (3 ml) followed by drying at 60°-70° C. (yield 7.1 gms, m.p. 129°-132° C. HPLC purity=97.0%, light creamish colored powder).

Example-21

Preparation of 5-Chloro-3-(4-methylsulphonyl)phenyl-2-(2-methyl-5-pyridyl)pyridine (I)

Compound of formula (IV) viz. 5-chloro-3-(4-methylthio) phenyl-2-(2-methyl-5-pyridyl)-pyridine (10 gms) was dissolved in dichloromethane (100 ml) and stirred at 25°-28° C. Sulphuric acid (0.94 gms) dissolved in water (0.5 ml) was added slowly to the above solution at 10°-15° C. A solution of sodium tungstate (0.17 gms) in water (1.5 ml) was then added gradually to it, followed by further addition of methyl-tri-n-octylammonium chloride (0.25 gms) and dichloromethane (2 ml). The reaction mass was then subjected to oxidation by gradual addition of 50% hydrogen peroxide solution (8.12 gms) in water (2 ml), while maintaining the reaction temperature at 12-14° C. over a period of approximately 1.5 to 2.0 hrs. The reaction temperature was gradually raised to 28°-30° C. and maintained for several hours while monitoring by TLC till reaction completion. Reaction mass was added with water (50 ml), and 10% sodium bicarbonate solution to maintain pH at 6.95-7.15. Dichloromethane layer containing product was separated and aqueous mass was extracted twice with dichloromethane (25 ml). Dichloromethane layers were mixed, washed twice with water (20 ml), dried over anhydrous sodium sulphate and treated with active carbon (0.8 gms). Filtered product solution was concentrated by distillation to obtained product residue. Solvent traces were removed by vacuum application and isopropanol (30 ml) was added. The mass was cooled to (−)2°-2° C. for a period of 2 hrs. Product was isolated by filtration, washed with cooled IPA (3 ml) followed by drying at 60°-70° C. (yield 7.5 gms, m.p. 131°-134° C. HPLC purity=96.89%, light creamish colored powder).

Example-22

Purification of 5-Chloro-3-(4-methylsulphonyl)phenyl-2-(2-methyl-5-pyridinyl)pyridine, Etoricoxib (I)

Etoricoxib (I), as obtained in example-19 was purified by crystallization form aqueous isopropanol. The compound (20 gms) was dissolved isopropanol (70 ml) containing 4% w/w water at reflux temperature under stirring. Activated carbon (1.9 gms) was added and the product solution was filtered after 15-20 minutes of reflux. Filtrate was cooled slowly to ambient temperature and then to 12°-15° C. for about 1 hour. Crystallized product was collected by filtration followed by washing with chilled isopropanol (5-10 ml). The mass was dried at 60°-70° C. to get light creamish product (yield 14.4 gms, m.p. 133°-137°, HPLC purity 99.10%).

Example-23

Purification of 5-Chloro-3-(4-methylsulphonyl)phenyl-2-(2-methyl-5-pyridinyl)pyridine, Etoricoxib (I)

Etoricoxib (I), as obtained in example 19 was purified by crystallization form aqueous isopropanol. The compound (20 gms) was dissolved isopropanol (90 ml) containing 4% w/w water at reflux temperature under stirring. Activated carbon (1.9 gms) was added and the product solution was filtered after 15-20 minutes of reflux. Filtrate was cooled slowly to ambient temperature and then to 12°-15° C. for about 1 hour. Crystallized product was collected by filtration followed by washing with chilled isopropanol (5-10 ml). The mass was dried at 60°-70° C. to get light creamish product (yield 14.0 gms, m.p. 134°-137°, HPLC purity 99.40%).

Example-24

Purification of 5-Chloro-3-(4-methylsulphonyl)phenyl-2-(2-methyl-5-pyridinyl)pyridine, Etoricoxib (I)

Etoricoxib (I), as obtained in example 19 was purified by crystallization form aqueous isopropanol. The compound (20 gms) was dissolved isopropanol (70 ml) containing 3% w/w water at reflux temperature under stirring. Activated carbon (1.9 gms) was added and the product solution was filtered after 15-20 minutes of reflux. Filtrate was cooled slowly to ambient temperature and then to 12°-15° C. for about 1 hour. Crystallized product was collected by filtration followed by washing with chilled isopropanol (5-10 ml). The mass was dried at 60°-70° C. to get light creamish product (yield 15.3 gms, m.p. 135°-137° C. HPLC purity 99.18%).

Example-25

Purification of 5-Chloro-3-(4-methylsulphonyl)phenyl-2-(2-methyl-5-pyridinyl)pyridine, Etoricoxib (I)

Etoricoxib (I), as obtained in example 19 was purified by crystallization form aqueous isopropanol. The compound (20 gms) was dissolved in mixture of isopropanol (60 ml)+Acetone (15 ml) containing 6% w/w water at reflux temperature under stirring. Activated carbon (1.9 gms) was added and the product solution was filtered after 15-20 minutes under reflux. Filtrate was cooled slowly to ambient temperature and then to 12°-15° C. for about 1 hour. Crystallized product was collected by filtration followed by washing with chilled isopropanol (5-10 ml). The mass was dried at 60°-70° C. to get light creamish product (yield 15 gms, m.p. 135°-137° C. HPLC purity 99.35%).

Example-26

Purification of 5-Chloro-3-(4-methylsulphonyl)phenyl-2-(2-methyl-5-pyridinyl)pyridine, Etoricoxib (I)

Etoricoxib (I) as obtained in example 19 (20 gms) was dissolved in ethyl acetate (110 ml) at ambient condition, under stirring. Paratoluenesulphonic acid (16 gms) was added to it slowly in small lots. The mass was heated to 55°-60° C. to obtain a clear solution and then treated with 0.5 gm active carbon for 15-20 minutes. The solution was filtered hot, and cooled under stirring to 10°-12° C. for a period of about one hour. Etoricoxib paratoluenesulphonic acid salt was isolated by filtration, washed with chilled ethyl acetate (10 ml-15 ml), and dried at 50°-60° till constant weight (yield 28 gm)

Etoricoxib-PTSA salt obtained above (28 gm) was added with water (250 ml) and stirred at ambient temperature for 15-20 minutes. Gradually 10% sodium bicarbonate solution was added till pH was around 7.90 to 8.10, followed by toluene (50 ml). The reaction mixture was heated to 50°-55° C., stirred for 10 minutes and allowed to stand. Toluene layer containing product was separated and the aqueous layer was extracted twice with toluene (80 ml) in a similar manner combined toluene layer was washed with water (100 ml), treated with active carbon (2.5 gms), dried over anhydrous sodium sulphate, filtered and concentrated at 60-65° C. under reduced pressure to obtain a residue. Isopropanol (94 ml) containing 4% water was added to the residue and it was heated to 55°-65° C. to dissolve. The solution was slowly cooled to ambient temperature and then to 5°-10° for 1.5 hrs. Product mass was filtered, washed with cold isopropanol (10 ml), and dried at 60°-65° C. till constant weight (yield 11 gms, m.p. 135°-137° C., HPLC purity=99.23%)

Example-27

Preparation of 5-Chloro-3-(4-methylsulphonyl)phenyl-2-(2-methyl-5-pyridinyl)pyridine, Etoricoxib (I)

Etoricoxib (I), as obtained in example 19 was (20 gm) was dissolved in isopropyl alcohol (70 ml)+water (4.20 ml) at reflux temperature under stirring. Activated carbon (1.9 gms) was added and the product solution was filtered after 15-20 minutes. Filtrate was cooled slowly to ambient temperature and then to 12°-15° C. for about 1 hour. Crystallized product was collected by filtration followed by washing with chilled isopropanol (5-10 ml). The mass was dried at 60°-70° C. to get light creamish product (yield 15.3 gms, m.p. 135°-137° C., HPLC purity 99.10%).

Example-28

Preparation of 5-Chloro-3-(4-methylsulphonyl)phenyl-2-(2-methyl-5-pyridinyl)pyridine, Etoricoxib (I)

Etoricoxib (I), as obtained in example 21 was (20 gm) was dissolved in pure ethanol (80 ml) at reflux temperature under stirring. Activated carbon (1.9 gms) was added and the product solution was filtered after 15-20 minutes. Filtrate was cooled slowly to ambient temperature and then to 12°-15° C. for about 1 hour. Crystallized product was collected by filtration followed by washing with chilled pure ethanol (5-10 ml). The mass was dried at 60°-70° C. to get light creamish product (yield 15.1 gms, m.p. 136°-138° C., HPLC purity 99.28%)

Example-29

Preparation of 1-(6-methyl-3-pyridinyl)-2-[(4-Methylsulphonyl)phenyl]ethanone (II)

4-Methyl thiobenzyl cyanide (20.0 gm) was dissolved is (100 ml) Toluene and reaction mass was refluxed. Methyl-6-methyl nicotinate (21.74 gm) was added slowly in 45 minutes. Sodium methoxide powder 12.0 gm was introduced within 30 mints. The reaction temp was maintained at reflux for about 4-6 hrs, till spot corresponding to methyl-6-methyl nicotinate is practically absent in TLC. The reaction mass was cooled to 25°-30° C. under stirring followed by slow addition in crushed ice (190 gm)+water (45 ml) mixture. The pH of reaction mass was adjusted between 5.2 to 6.2 with dilute hydrochloric acid, and stirred for an hour, filtered, washed with water and suck dried on a Buchner funnel. This wet product mass of 1-(6-methyl-3-pyridinyl)-2-cyano-2-[(4-Methylthio)phenyl]ethanone (VI) was added to a mixture of concentrate hydrochloric acid (140 ml) and glacial acetic acid (60 ml) at 40°-50° C. temp, followed by decarboxylation at reflux temperature. Reaction mass was cooled to room temperature once reaction was complete as indicated by TLC and was washed by extracting with hexane. The above reaction mass was slowly poured in to mixture of (70 ml) concentrate ammonia solution and (25.00 ml) water. Reaction mass was stirred for 10 minutes and pH was adjusted between 6.80 to 7.20 with dilute ammonia solution at 0-5° C. Product mass was maintained for 30 minutes and filtered. The product obtained was washed with water, and was spin dried.

Product (wet) mass of 1-(6-methyl-3-pyridinyl)-2-[(4-Methylthio)phenyl]ethanone (V) was dissolved in dichloromethane (185 ml), stirred allowed to settle and aqueous layer was separated. Dichloromethane solution of the product was directly forwarded to the subsequent synthetic stage of oxidation with a mixture of concentrate Sulphuric acid (4.10 gm.)+water (4.50 ml) and stirred for 15-20 minutes. A solution of sodium tungstate (0.74 gm) in water (14.0 ml) was also charged and reaction mass was stirred for 10 minutes followed by addition of mixture of methyl-tri-n-octyl chloride (0.80 gm) in dichloromethane (8.0 ml). The reaction mixture was stirred for 10 minutes, and cooled to 18°-20° C. Mixture of 50% Hydrogen peroxide (19.50 gm) and water (12.50 ml) was gradually added within 45 minutes at 18°-20° C. temp. Reaction mass was maintained for several hours and monitored by TLC examination, till the spot corresponding to 1-(6-methyl-3-pyridinyl)-2-[(4-methylthio)phenyl]ethanone (V) was practically absent by TLC. Reaction mass pH was set between 6.95 to 7.10 using mixture of diluted ammonia solution under string within 30 minutes at 25°-30° C. It was stirred for 10 minutes, aqueous layer separated and extracted with dichloromethane (130 ml). Combined dichloromethane layer containing product was washed with water (110 ml), dried over anhydrous sodium sulphate and filtered. Dichloromethane at atmospheric pressure to obtained. Vacuum was finally applied and the mass was degassed Then isopropyl alcohol (96 ml) was added, stirred mass and cooled to 25°-30° C. followed by chilling to 0°-5° C. temp, maintained for an hour, filtered, washed with chilled isopropyl alcohol and dried at 50°-60° C. (yield 21 gms, m.p. 176°-180° C., purity by HPLC-92.50%).

We claim:

1. A process for the preparation of etoricoxib comprising subjecting 5-Chloro-3-(4-methylthio)phenyl-2-(2-methyl-5-pyridinyl)pyridine (IV) to oxidation in presence of an oxidation catalyst, a phase transfer catalyst, and a halogenated hydrocarbon solvent to obtain etoricoxib of formula-(I);

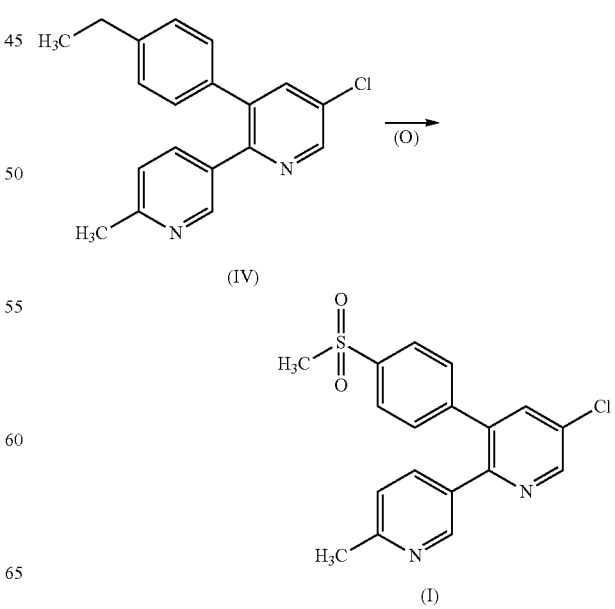

wherein the oxidation catalyst is selected from the group consisting of molybdenum, vanadium, and tungsten catalysts; and
wherein the phase transfer catalyst is selected from the group consisting of quatenary ammonium chloride salts.

2. The process according to claim 1, wherein the oxidation catalyst is selected from the group consisting of sodium molybdate, sodium vanadate and sodium tungstate.

3. The process according to claim 1, wherein the phase transfer catalyst is selected from the group consisting of methyl-tri-n-octyl ammonium chloride, methyl-tri-n-butyl ammonium chloride, benzethonium chloride, and methyl benzethonium chloride.

4. The process according to claim 1, wherein the oxidation is carried out in the presence of hydrogen peroxide or sodium peroxide.

5. The process according to claim 1, wherein the halogenated hydrocarbon solvent is selected from the group consisting of chloroform, dichloromethane, dichloroethane or carbon tetrachloride; and the process is conducted in a biphasic system comprising the halogenated hydrocarbon solvent and water.

6. A process for the preparation of etoricoxib, comprising:
oxidizing 5-Chloro-3-(4-methylthio)phenyl-2-(2-methyl-5-pyridinyl)pyridine in a biphasic system comprising water and at least one halogenated hydrocarbon selected from the group consisting of chloroform, dichloromethane, dichloroethane or carbon tetrachloride;
said oxidizing being performed in the presence of:
an oxidation catalyst selected from the group consisting of molybdenum, vanadium, and tungsten catalysts; and
a phase transfer catalyst selected from the group consisting of quartenary ammonium chloride salts.

7. A process for the preparation of etoricoxib of formula-(I), comprising:
a) condensing 4-methylthio-benzylcyanide and methyl-6-methylnicotinate in the presence of a base and a solvent under reflux to obtain a compound of formula (VI);

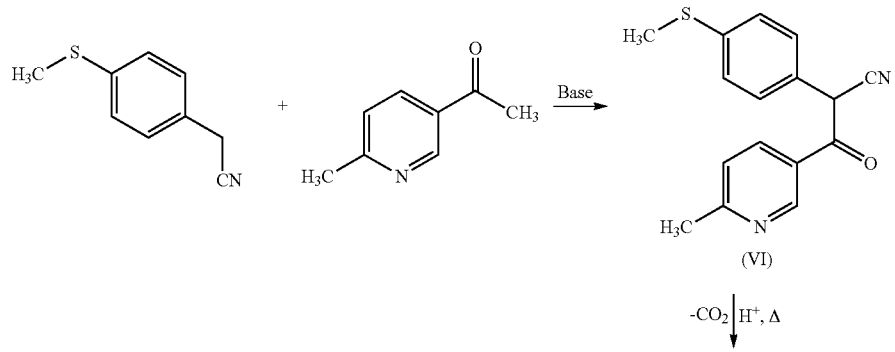

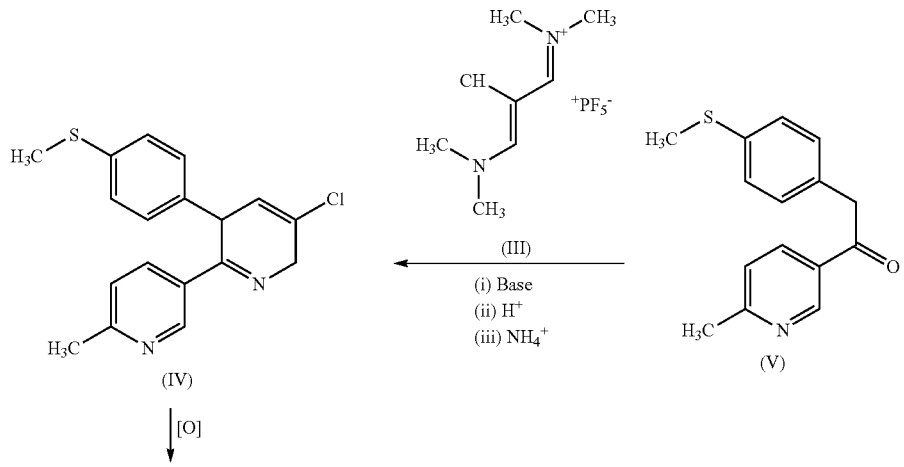

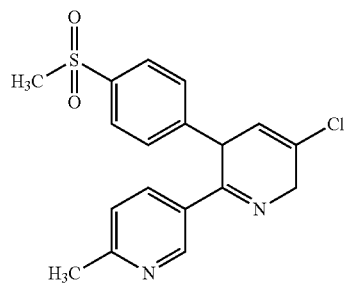

b) hydrolyzing the compound of formula (VI) in the presence of an acid at 40° to 50° C., followed by decarboxylating in situ under reflux to obtain a compound of formula (V);

c) reacting the compound of formula (V) with 2-chloro-N,N-dimethylamino trimethinium hexafluoro phosphate salt (III) in the presence of base and an organic solvent, followed by addition of alcohol and acid, adding an aqueous solution of ammonia followed by addition of an $NH_4^+$ salt, and heating under reflux to obtain a compound of formula (IV); and d) oxidizing the compound of formula (IV) in a halogenated hydrocarbon solvent, in the presence of:
   an oxidation catalyst selected from the group consisting of molybdenum, vanadium, and tungsten catalysts; and
   a phase transfer catalyst selected from the group consisting of quarternary ammonium chloride salts to obtain etoricoxib of formula (I).

8. The process according to claim 7, wherein the base for step (a) is selected from the group consisting of sodium methoxide, potassium methoxide, sodium amide, sodium hydride, and potassium tert-butoxide.

9. The process according to claim 7, wherein the solvent for step (a) is selected from the group consisting of heptane, toluene, xylene and mixtures thereof.

10. The process according to claim 7, wherein the hydrolysis in step (b) is conducted in a mixture of an organic acid and a mineral acid;
said organic acid being selected from the group consisting of formic acid, glacial acetic acid, propionic acid, butyric acid, pentanoic acid, and mixtures thereof.

11. The process according to claim 10, wherein the mineral acid is selected from the group consisting of concentrated hydrochloric acid and concentrated sulphuric acid.

12. The process according to claim 7, wherein the base for step (c) is selected from the group consisting of sodium methoxide, potassium methoxide, potassium tert-butoxide, sodium amide and sodium hydride.

13. The process according to claim 7, wherein the organic solvent for step (c) is selected from the group consisting of tert-butanol, isopropanol, tetrahydrofuran and methyl-tert-butyl ether.

14. The process according to claim 7, wherein the acid for step (c) is selected from the group consisting of formic acid, acetic acid, n-propionic acid and n-butyric acid.

15. The process according to claim 7, wherein the oxidation for step (d) is carried out in the presence of hydrogen peroxide or sodium peroxide.

16. The process according to claim 7, wherein step (d) is conducted in a biphasic system comprising a halogenated hydrocarbon and water;
said halogenated hydrocarbon being selected from the group consisting of chloroform, dichloromethane, dichloroethane, carbon tetrachloride, and mixtures thereof.

* * * * *

UNITED STATES PATENT AND TRADEMARK OFFICE
CERTIFICATE OF CORRECTION

| | | |
|---|---|---|
| PATENT NO. | : 8,841,457 B2 | Page 1 of 1 |
| APPLICATION NO. | : 13/885522 | |
| DATED | : September 23, 2014 | |
| INVENTOR(S) | : Shah et al. | |

It is certified that error appears in the above-identified patent and that said Letters Patent is hereby corrected as shown below:

In the Claims,

In claim 1, at col. 24, ll. 43-53, the structure corresponding to 5-Chloro-3-(4-methythio) phenyl-2-(2-methyl-5-pyridinyl) pyridine of Formula (IV) should appear as follows:

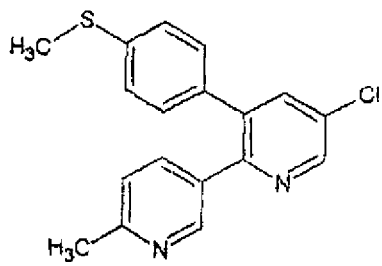

(IV)

Signed and Sealed this
Ninth Day of December, 2014

Michelle K. Lee
*Deputy Director of the United States Patent and Trademark Office*